United States Patent
Gao et al.

(10) Patent No.: US 7,700,817 B2
(45) Date of Patent: Apr. 20, 2010

(54) CATALYTIC CRACKING OF ETHERS TO 1-OLEFINS

(75) Inventors: Xiaoliang Gao, Calgary (CA); Stacy David Ross Johnston, Calgary (CA)

(73) Assignee: NOVA Chemicals (International) S.A. (CH)

( * ) Notice: Subject to any disclaimer, the term of this patent is extended or adjusted under 35 U.S.C. 154(b) by 2 days.

(21) Appl. No.: 12/011,878

(22) Filed: Jan. 30, 2008

(65) Prior Publication Data

US 2008/0194899 A1 Aug. 14, 2008

(30) Foreign Application Priority Data

Feb. 14, 2007 (CA) .................... 2578494

(51) Int. Cl.
*C07C 1/00* (2006.01)
(52) U.S. Cl. ........................ 585/640; 585/639
(58) Field of Classification Search ........... 585/639, 585/640
See application file for complete search history.

(56) References Cited

U.S. PATENT DOCUMENTS 4,234,752 A    11/1980  Wu et al.
7,342,144 B2 *  3/2008  Kaizik et al. ............... 585/640
2003/0065233 A1  4/2003  Fuji et al.
2006/0036121 A1  2/2006  Kaizik et al.

FOREIGN PATENT DOCUMENTS

EP         0 440 995 B1    5/1994
WO         WO 92/10450 A1  6/1992

OTHER PUBLICATIONS

Herman Pines et al., Journal of the American Chemical Society, 1960, v82, pp. 2401-2402.
Herman Pines et al., Journal of the American Chemical Society, 1960, v82, pp. 2471-2483.
Herman Pines et al., Journal of the American Chemical Society, 1961, v83, pp. 2847-2852.
Herman Pines et al., Journal of the American Chemical Society, 1961, v83, pp. 3270-3274.

* cited by examiner

*Primary Examiner*—In Suk Bullock
(74) *Attorney, Agent, or Firm*—Kenneth H Johnson

(57) ABSTRACT

The current invention provides a process in which ethers are converted into α-olefins by passage over a modified alumina catalyst. The alumina catalyst is made by treating gamma-alumina with a rare earth metal oxide such as lanthanum oxide, $La_2O_3$. The modified aluminum catalysts convert 1-methoxyoctane into 1-octene with high selectivity at high conversion rates.

9 Claims, No Drawings

CATALYTIC CRACKING OF ETHERS TO 1-OLEFINS

FIELD OF THE INVENTION

The present invention provides rare earth oxide treated alumina catalysts which convert ethers into terminal, 1-olefins.

BACKGROUND OF THE INVENTION

The dehydration of alcohols using a heterogeneous alumina catalyst is a well known chemical transformation. Early work on this reaction showed that alcohols could be converted into their corresponding olefins, without extensive isomerization, if base treated alumina was used as a catalyst. See for example, Herman Pines et. al. in the *Journal of the American Chemical Society*, 1960, v82, at pages 2401 and 2471 and Herman Pines et. al. in the *Journal of the American Chemical Society*, 1961, v83 at pages 2847 and 3270. The authors treated alumina with sodium hydroxide, ammonia, methylammonia and pipyridine and found that, the stronger the base used, the smaller the degree of isomerization observed. Hence by rendering an alumina catalyst less acidic, isomerization of product olefins was suppressed.

The patent literature discloses several methods to produce olefins from both the dehydration of alcohols or the cracking of ethers using a base modified alumina catalyst.

For example, U.S. Pat. No. 4,234,752 to Phillips Petroleum Company discloses that linear or branched alcohols containing from 2 to about 20 carbon atoms can be converted to olefins by dehydration over a base modified gamma-alumina catalyst. In one embodiment, 3-methyl-1-butanol was converted to 3-methyl-1-butene with over 90% yield. Excessive acidic sites in the alumina were neutralized with sodium hydroxide or potassium hydroxide.

US Patent Application, 2003/0065233 to Kuraray Co. describes a process for making α-olefins from primary alcohols or ethers through elimination reactions catalyzed by a modified alumina catalyst. The alumina catalyst was modified with an organic amine.

Similarly, US Patent application 2006/0036121 to Oxeno discloses a base catalyzed process for the production of α-olefins from ethers ("1-alkoxyalkanes"). The catalysts used were alumina or zirconia catalysts which had been treated with alkali and/or alkali earth oxides. In a preferred embodiment 1-methoxyoctane is converted to 1-octene with 94.2% selectivity at a conversion of about 83.7%.

Cracking processes, such as those which convert ethers to α-olefins may play a significant role in the final stages of converting butadiene to 1-octene, an α-olefin of significant commercial utility, particularly to the plastics, surfactants and lubricants industries.

For example, WO 92/10450 describes a process in which 1,3-butadiene is converted first to 2,7-octadienyl ether over a palladium catalyst in the presence of methanol. The 2,7-octadienyl ether is then hydrogenated to 1-methoxyoctane which is cleaved over alumina to provide 1-octene. Alternatively, butadiene may be reacted with a carboxylic acid instead of methanol in the first step according to EP 0,440,955. The selectivity of the ether cleavage step in each of these processes is poor at high conversions, due to acidic alumina sites which not only catalyze the ether cleavage reaction, but also contribute to isomerization of the product α-olefins to internal olefins.

There remains a need for new catalysts which crack ethers into 1-olefins with an improved combination of selectively and conversion.

The current invention provides a process in which ethers are converted to α-olefins with high selectivity at high conversions using an alumina catalyst which has been treated with a rare earth metal oxide.

The current invention also provides modified alumina catalysts in which selectivity to 1-olefins as well as conversion rates are relatively insensitive to the loading of the rare earth metal oxide. Hence, preparation of the inventive catalysts is facile and requires little optimization.

SUMMARY OF THE INVENTION

Provided is a process to crack one or more ethers into their corresponding α-olefins over a gamma-alumina catalyst, wherein said gamma-alumina catalyst is modified with a rare earth metal oxide.

In a preferred embodiment, 1-octene is selectively produced from 1-methoxyoctane using a gamma-alumina catalyst which has been modified with lanthanum oxide.

DETAILED DESCRIPTION

The current invention generally relates to the production of α-olefins from ethers using a modified gamma-alumina catalyst.

We have discovered that the use of alumina catalysts which are modified with a rare earth metal oxide are capable of cracking ethers into their corresponding α-olefins with high selectivity at high conversions. The term α-olefin or "alpha" olefin is well known in the art and connotes a terminal olefin or a 1-olefin, in which the double bond resides only at the terminal position (as opposed to an internal olefin, in which the double bond is at an internal site).

Without wishing to be bound by theory, it is desirable to modify alumina catalysts such that the acidic sites of the alumina are neutralized with regard to isomerization catalysis, but not with regard to catalytic cracking behavior. That acidic sites catalyze the isomerization of terminal olefins is well known in the art (see for example, Herman Pines et. al. in the *Journal of the American Chemical Society*, 1960, v82 at page 2471). Hence, treatment with base may require lengthy and involved optimization protocols to find a good balance of selectivity and conversion. By way of example, when using alkali metal oxides such as $Na_2O$ or $K_2O$ to modify the alumina, small changes in oxide loading (as little as 0.25 wt %) can lead to large changes in selectivity to α-olefins as well as to large swings in the conversion rates.

In contrast, in the current invention, use of $La_2O_3$, a rare earth metal oxide to modify alumina allows for a good balance or selectivity and conversion over a larger range of oxide loadings. As a result, it is simple to optimize and manipulate the performance of the modified alumina catalysts of the present invention.

The catalysts used in the current invention are derived from alumina ($Al_2O_3$). The alumina used is preferably "gamma" form or γ-alumina. The term "gamma-alumina" or "γ-alumina", means that the alumina is predominately in the gamma crystal form as determined by x-ray crystallography. Gamma-alumina is readily available from commercial suppliers. Gamma-aluminas may be purchased in different forms (e.g. particulates or extrudates), particle sizes, surface areas, and pore sizes and pore volumes. The choice of the most preferred type of gamma-alumina will be influenced by conventional design considerations, including the cost of the commercially available gamma-alumina products and the configuration of the cracking reactor.

The γ-alumina will have a BET surface area of from 50 to 400 m$^2$/g, preferably from 100 to 350 m$^2$/g as measured according to ASTM D1993-03.

The alumina is modified with a rare earth metal oxide, preferably lanthanum oxide, $La_2O_3$ prior to use as a cracking catalyst. It will be understood by a person skilled in the art, that the lanthanum oxide may be conveniently generated by adding hydrated lanthanum nitrate, $La(NO_3)$ to the alumina and that lanthanum oxide, $La_2O_3$ forms in situ. Other suitable sources of lanthanum oxide are also contemplated for use with the current invention. For example, as $La(OH)_3$ may be used.

The lanthanum oxide, $La_2O_3$ can be loaded onto the alumina in from 0.01 to 10 wt %. In an embodiment of the current invention, the $La_2O_3$ is loaded onto the alumina in from 0.1 to 3 wt %.

As further components, the catalysts of the current invention may comprise titanium dioxide, silicon dioxide, iron oxide and/or small amounts of thorium oxide.

The modified γ-alumina catalysts are prepared according to known methods. For example wet-incipient method, precipitation, and spray-drying techniques may be used.

In the current invention, one or more ethers are converted by catalytic cracking, primarily to terminal, 1-olefins by passage over the modified alumina catalyst. The one or more ethers used in the present invention are ethers having the general formula R—O—R' where R and R' are selected from the group consisting of a linear or branched alky group. In one embodiment of the current invention, R is selected from a group consisting of methyl, ethyl, and n-propyl and R' is an alky group having 4 to 18 carbon atoms. In a particular embodiment of the invention, the one or more ethers is substantially 1-methoxyoctane (i.e. R=Methyl; R'=octyl). The use of the phrase "substantially 1-methoxyoctane" means that 1-methoxyoctane comprises at least 90% by weight of the one or more ethers.

In the process of the current invention, the conversion of ethers to α-olefins is preferably carried out in the gas phase but may also be carried out in a mixed liquid/gas phase.

Cracking of ethers may be carried out in a batch mode or a continuous mode over a heterogeneous catalyst. In a preferred embodiment of the current invention, a continuous mode is used in which the ethers are passed over the modified alumina catalyst in a fixed bed reactor. The modified alumina catalyst may be suspended or in particulate form.

The one or more ethers of the current invention will be added to the reactor at weight hourly space velocity (WHSV, as reported in grams of reactant per gram of catalyst per hour) of from between 0.01 and 30 reciprocal hours (hr$^{-1}$). In a particular embodiment of the invention, the WHSV will be from 5 to 15 hr$^{-1}$.

The process of the current invention may be used in the presence or absence of inert gases or substances. By the term "inert" it is meant that the gases or substances are un-reactive under the conditions used to crack the ethers. Some non-limiting examples of such inert gases include helium, nitrogen and argon. Substances such as methane, propane, dimethyl ether, and steam are also contemplated for use with the current invention, provided they are un-reactive under cracking conditions.

The amount of inert carrier gas is not critical to the invention, but as a practical guide, an amount from about 0.1 to 1000, preferably, 0.5 to 300 liters of inert carrier gas per kilogram of ether may be used.

Ethers may be cracked using reaction temperatures of from 100° C. to 600° C., preferably from 200° C. to 400° C. Typical pressures for use with the process of the invention range from 0.1 to 40 bar. In another embodiment, the pressure will be from 1 to 10 bar.

In the current invention, the process may be carried out under high or low conversion conditions. Unconverted ethers can be recycled back to the reactor after removal of product olefins. Preferably, the conversion of ethers to cracked products will be more than 75%.

The product α-olefins of the inventive process are formed with high selectivity and high conversions, however if necessary, they may be separated from un-reacted ethers or bi-products by methods well known to those skilled in the art, such as for example, distillation, extraction, scrubbing and the like.

The invention will be further illustrated by the following examples. The examples are intended to be illustrative only and are not intended to limit the scope of the invention in any way.

EXAMPLES

Cracking reactions were performed in a fixed bed tubular reactor. There were two separate heating zones in the system. The first zone, 4" in length, was controlled at about 300° C. to vaporize the feed liquid and to maintain the vapor temperature close to the reaction temperature. The second zone contained a reactor having dimensions of 0.402" internal diameter×2" length. Both zones were controlled by independent thermocouples and temperature-control units. A catalyst was loaded in the reactor, which was heated at 300° C. overnight under a slow stream of nitrogen. The ether (1-methoxyoctane or "MOAN") was fed into the reactor at the top with a syringe pump. The product stream was passed through a condenser and the liquid was collected for analysis by gas chromatography (Agilent 6890). Under normal circumstances, the MOAN was fed at a given WHSV for 0.5 hr before the first sample was collected. After sampling, if a change of WHSV or reaction temperature was needed, the reactor was stabilized again for another 0.5 hr before the next sample was collected. In the process, no sweep gas was required. Vaporization of the MOAN feed pushes the products through the catalyst bed and the reactor.

Example 1

An unmodified γ-aluminum catalyst was used as a comparative example. The high purity alumina was purchased from Sasol as Alumina Extrudate Type A. ($La_2O_3$, 0 ppm; $Na_2O$, 36 ppm; $Fe_2O_3$, 287 ppm; $SiO_2$, 214 ppm; loose bulk density, 0.46 g/mL; median diameter, 1.65 mm; median length, 4 mm; Loss of Ignition (L.O.I), 2.5%; surface area, 142 M$^2$/g; side crushing strength, 28 N; pore volume, total (Hg), 0.9 ml/g; median pore size, 99 Angstrom). Details of the MOAN cracking reactions using the unmodified gamma-aluminum catalyst are provided in Table 1.

Example 2

Sasol Alumina Extrudate Type C was purchased from Sasol. Alumina Extrudate Type C is composed of 97.1 wt % $Al_2O_3$ and 2.9 wt % $La_2O_3$. Also present in Alumina Extrudate Type C are $Na_2O$ (76 ppm), $Fe_2O_3$ (130 ppm) and $SiO_2$ (116 ppm). Other parameters include: loose bulk density, 0.57 g/mL; median diameter, 1.63 mm; median length, 4.9 mm; Loss of Ignition (L.O.I), 1.9%; surface area, 143 M$^2$/g; side crushing strength, 57 N; pore volume, total (Hg), 0.61 ml/g; median pore size, 60 Angstrom. The data provided in Table 2, show that high selectivity for 1-octene is achieved, but the conversion of MOAN is low.

Examples 3-5

The inventive catalysts were prepared by impregnating high purity gamma-alumina with $La(NO_3)_3$ by wet incipient method, followed by calcination at 550° C. overnight. The high purity gamma-alumina extrudates were purchased from Sasol as Alumina Extrudate Type A. ($La_2O_3$, 0 ppm; $Na_2O$, 36 ppm; $Fe_2O_3$, 286 ppm; $SiO_2$, 214 ppm; loose bulk density, 0.46 g/mL; median diameter, 1.65 mm; median length, 4 mm; L.O.I, 2.5%; surface area, 142 $M^2$/g; side crushing strength, 28 N; pore volume, total (Hg), 0.9 ml/g; median pore size, 99 Angstrom). The alumina extrudates were crushed to 20-40 mesh prior to any modification.

Three modified alumina catalysts were made. The loadings of $La_2O_3$ were 0.5 wt %, 0.75 wt % and 1.0 wt % respectively. The results of cracking MOAN to produce 1-octene are shown in Tables 3-5.

For commercial production of 1-octene, the selectivity to 1-octene should be at least 95% to minimize loss to unwanted internal octenes. Table 1 shows that for unmodified alumina, the selectivity to 1-octene lies between 91-92% at very high MOAN conversion.

For alumina modified with 1 wt % of $La_2O_3$ (Table 3), the selectivity to 1-octene increased to over 96% at reasonable MOAN conversions (76-81%). When the loading of $La_2O_3$ decreased to 0.5 wt % (Table 4), the selectivity of 1-octene dropped slightly to 94-95% while MOAN conversion increased to 90-91%. Adjusting the $La_2O_3$ loading to 0.75% brought the selectivity to about 96% with good MOAN conversion (Table 5).

Note that for the first sample for each run in Tables 1, 3-5, the system was not completely stabilized and therefore the data shown for the first sample (i.e. first row) for each run are not necessarily representative of the actual performance of the current inventive catalysts.

The results in Tables 3-5 clearly show that $La_2O_3$ is a good modifier for gamma-alumina with regard to enhancing 1-octene selectivity in the production of 1-octene from 1-methoxyoctane.

TABLE 1

Cracking MOAN Over Unmodified Alumina

| Run # | Sample | Time on line | WHSV ($h^{-1}$) | Flow (ml/hr) | MOAN Conversion (%) | Selectivity To Octenes (%) | 1-Octene Selectivity (%) | Di-N-Octylether (%) | Dimethylether (%) | Methanol (%) | n-Octanol (%) | Other products |
|---|---|---|---|---|---|---|---|---|---|---|---|---|
| 109 | A | 2 | 10 | 21 | 99.88 | 96.74 | 44.82 | 0.02 | 0.07 | 0.01 | 0.01 | 3.15 |
|  | B | 4 | 10 | 21 | 99.95 | 96.83 | 76.22 | 0.01 | 4.26 | 0.46 | 0.01 | 2.94 |
|  | C | 6 | 10 | 21 | 99.20 | 96.61 | 92.26 | 0.01 | 3.48 | 0.43 | 0.13 | 3.01 |
|  | D | 8 | 10 | 21 | 99.27 | 97.01 | 92.25 | 0.01 | 4.26 | 0.48 | 0.12 | 2.63 |
|  | E | 10 | 10 | 21 | 99.43 | 96.94 | 91.22 | 0.02 | 0.40 | 0.04 | 0.10 | 2.81 |
|  | F | 12 | 10 | 21 | 99.08 | 96.79 | 91.88 | 0.01 | 0.16 | 0.01 | 0.16 | 2.91 |
|  | G | 14 | 10 | 21 | 99.05 | 96.86 | 91.85 | 0.01 | 3.65 | 0.43 | 0.15 | 2.75 |
|  | H | 16 | 10 | 21 | 98.72 | 96.65 | 92.01 | 0.01 | 3.14 | 0.39 | 0.20 | 2.89 |
|  | I | 18 | 10 | 21 | 99.76 | 96.83 | 89.00 | 0.02 | 3.25 | 0.36 | 0.04 | 2.92 |
|  | J | 19.5 | 12 | 25.2 | 99.20 | 97.16 | 91.39 | 0.01 | 2.47 | 0.31 | 0.13 | 2.52 |
|  | K | 21 | 14 | 29.4 | 98.94 | 96.95 | 91.59 | 0.02 | 0.00 | 0.00 | 0.18 | 2.71 |
|  | L | 22.25 | 16 | 33.6 | 98.87 | 97.42 | 91.60 | 0.00 | 2.99 | 0.38 | 0.17 | 2.21 |

TABLE 2

Cracking MOAN Over Sasol Alumina Extrudate Type C

| Run # | Sample | Time on line | WHSV ($h^{-1}$) | Flow (ml/hr) | MOAN Conversion (%) | Selectivity To Octenes (%) | 1-Octene Selectivity (%) | Di-N-Octylether (%) | Dimethylether (%) | Methanol (%) | n-Octanol (%) | Other products |
|---|---|---|---|---|---|---|---|---|---|---|---|---|
| 110 | E | 10 | 10 | 21 | 57.98 | 85.79 | 97.97 | 2.43 | 4.54 | 1.89 | 3.32 | 1.53 |

TABLE 3

Cracking MOAN Over Alumina Modified With 1 wt % of $La_2O_3$

| Run # | Sample | Time on line | WHSV ($h^{-1}$) | Flow (ml/hr) | MOAN Conversion (%) | Selectivity To Octenes (%) | 1-Octene Selectivity (%) | Di-N-Octylether (%) | Dimethylether (%) | Methanol (%) | n-Octanol (%) | Other products |
|---|---|---|---|---|---|---|---|---|---|---|---|---|
| 116 | A | 1.5 | 10 | 20.8 | 97.89 | 96.79 | 89.37 | 0.04 | 1.44 | 0.22 | 0.23 | 2.01 |
|  | B | 3 | 10 | 20.8 | 81.29 | 93.88 | 96.69 | 0.66 | 1.78 | 0.81 | 2.10 | 1.88 |
|  | C | 4.5 | 10 | 20.8 | 79.28 | 93.18 | 96.83 | 0.84 | 2.37 | 0.96 | 2.27 | 1.91 |
|  | D | 6 | 10 | 20.8 | 76.95 | 92.60 | 96.91 | 1.01 | 2.43 | 1.04 | 2.43 | 1.87 |
|  | E | 7.5 | 10 | 20.8 | 78.04 | 92.85 | 96.82 | 0.93 | 3.75 | 1.20 | 2.33 | 1.83 |
|  | F | 9 | 10 | 20.8 | 80.28 | 93.73 | 96.45 | 0.74 | 3.01 | 1.04 | 2.15 | 1.83 |
|  | G | 10.5 | 10 | 20.8 | 77.59 | 92.94 | 96.72 | 0.91 | 3.41 | 1.12 | 2.33 | 1.78 |
|  | H | 12 | 10 | 20.8 | 76.91 | 92.50 | 96.71 | 0.99 | 4.03 | 1.25 | 2.38 | 1.88 |
|  | I | 13.5 | 10 | 20.8 | 76.43 | 92.52 | 96.63 | 1.04 | 2.03 | 0.96 | 2.45 | 1.87 |

TABLE 4

Cracking MOAN Over Alumina Modified With 0.5 wt % of $La_2O_3$

| Run # | Sample | Time on line | WHSV ($h^{-1}$) | Flow (ml/hr) | MOAN Conversion (%) | Selectivity To Octenes (%) | 1-Octene Selectivity (%) | Di-N-Octylether (%) | Dimethylether (%) | Methanol (%) | n-Octanol (%) | Other products |
|---|---|---|---|---|---|---|---|---|---|---|---|---|
| 117 | A | 1.5 | 10 | 20.7 | 99.87 | 96.90 | 71.25 | 0.04 | 3.55 | 0.40 | 0.01 | 1.82 |
| | B | 3 | 10 | 20.7 | 94.63 | 96.23 | 93.73 | 0.06 | 3.69 | 0.62 | 0.70 | 2.25 |
| | C | 4.5 | 10 | 20.7 | 92.30 | 95.89 | 95.04 | 0.15 | 0.39 | 0.12 | 1.07 | 2.24 |
| | D | 6 | 10 | 20.7 | 91.42 | 95.60 | 95.14 | 0.22 | 2.31 | 0.55 | 1.15 | 2.25 |
| | E | 7.5 | 10 | 20.7 | 93.02 | 95.97 | 94.83 | 0.15 | 1.85 | 0.44 | 0.97 | 2.22 |
| | F | 9 | 10 | 20.7 | 88.41 | 95.53 | 95.02 | 0.36 | 1.08 | 0.34 | 1.35 | 1.96 |
| | G | 10.5 | 10 | 20.7 | 91.17 | 95.63 | 94.96 | 0.24 | 3.18 | 0.68 | 1.17 | 2.16 |
| | H | 12 | 10 | 20.7 | 91.51 | 95.83 | 94.86 | 0.18 | 1.04 | 0.28 | 1.12 | 2.18 |
| | I | 13.5 | 10 | 20.7 | 91.43 | 95.77 | 94.82 | 0.20 | 0.95 | 0.28 | 1.15 | 2.21 |
| | J | 15 | 10 | 20.7 | 90.86 | 95.72 | 94.82 | 0.20 | 1.65 | 0.46 | 1.19 | 2.15 |
| | K | 16.5 | 10 | 20.7 | 91.88 | 95.92 | 94.60 | 0.16 | 3.39 | 0.64 | 1.06 | 2.10 |
| | L | 18 | 10 | 20.7 | 90.80 | 95.63 | 94.67 | 0.22 | 1.02 | 0.33 | 1.21 | 2.21 |
| | M | 19.5 | 10 | 20.7 | 90.87 | 95.72 | 94.61 | 0.20 | 3.06 | 0.64 | 1.18 | 2.10 |
| | N | 21 | 10 | 20.7 | 91.09 | 95.67 | 94.42 | 0.20 | 0.82 | 0.27 | 1.18 | 2.24 |
| | O | 22.5 | 10 | 20.7 | 90.28 | 95.50 | 94.49 | 0.26 | 2.71 | 0.64 | 1.24 | 2.15 |

TABLE 5

Cracking MOAN Over Alumina Modified With 0.75 wt % of $La_2O_3$

| Run # | Sample | Time on line | WHSV ($h^{-1}$) | Flow (ml/hr) | MOAN Conversion (%) | Selectivity To Octenes (%) | 1-Octene Selectivity (%) | Di-N-Octylether (%) | Dimethylether (%) | Methanol (%) | n-Octanol (%) | Other products |
|---|---|---|---|---|---|---|---|---|---|---|---|---|
| 121 | A | 1.5 | 10 | 20.5 | 99.81 | 96.87 | 77.33 | 0.01 | 2.74 | 0.30 | 0.01 | 1.84 |
| | B | 3 | 10 | 20.5 | 87.59 | 94.79 | 96.02 | 0.41 | 2.31 | 0.74 | 1.58 | 2.19 |
| | C | 4.5 | 10 | 20.5 | 84.45 | 94.33 | 96.11 | 0.59 | 0.01 | 0.02 | 1.85 | 2.11 |
| | D | 6 | 10 | 20.5 | 83.01 | 93.89 | 96.31 | 0.71 | 2.34 | 0.88 | 2.02 | 1.98 |
| | E | 7.5 | 10 | 20.5 | 82.54 | 93.72 | 96.25 | 0.76 | 2.20 | 0.87 | 2.07 | 2.00 |
| | F | 9 | 10 | 20.5 | 83.89 | 93.90 | 95.90 | 0.66 | 2.33 | 0.86 | 1.97 | 2.11 |
| | G | 10.5 | 10 | 20.5 | 81.61 | 93.32 | 95.93 | 0.83 | 3.19 | 1.03 | 2.17 | 2.03 |
| | H | 12 | 10 | 20.5 | 81.39 | 93.37 | 95.70 | 0.86 | 1.04 | 0.67 | 2.22 | 2.04 |
| | I | 13.5 | 10 | 20.5 | 79.24 | 93.07 | 95.67 | 0.92 | 1.26 | 0.77 | 2.36 | 1.92 |
| | J | 15 | 10 | 20.5 | 79.71 | 93.05 | 95.49 | 0.94 | 0.97 | 0.71 | 2.36 | 1.97 |
| | K | 16.5 | 10 | 20.5 | 75.80 | 92.81 | 96.00 | 0.87 | 2.63 | 1.24 | 2.25 | 1.91 |

What is claimed is:

1. A process to crack one or more than one ether into its corresponding α-olefin over a gamma-alumina catalyst, wherein said gamma-alumina catalyst is modified with 0.5 to 10 wt % lanthanum oxide.

2. A process according to claim 1, wherein the one or more than one ether is an ether having the general formula R—O—R', where R is selected from the group consisting of methyl, ethyl, and n-propyl; and R' is an alky group having 4 to 18 carbon atoms.

3. A process according to claim 2, which takes place in a gas phase.

4. A process according to claim 3, which takes place at from 200 ° C. to 400° C. degrees.

5. A process according to claim 4, which takes place at a pressure of from 1 to 10 bar.

6. A process according to claim 5, wherein the one or more than one ether is substantially 1-methoxyoctane.

7. A process according to claim 6, wherein the WHSV is from 5 to 15 $hr^{-1}$.

8. A process according to claim 7, wherein 1-methoxyoctane is cracked to 1-octene with more than 94% selectivity.

9. A process according to claim 8, wherein the conversion of 1-methoxyoctane is from 75% to 93%.

* * * * *